United States Patent [19]
Sword

[11] Patent Number: 6,122,967
[45] Date of Patent: Sep. 26, 2000

[54] FREE MOTION SCANNING SYSTEM

[75] Inventor: Charles K. Sword, Pleasant Hills, Pa.

[73] Assignee: The United States of America as represented by the United States Department of Energy, Washington, D.C.

[21] Appl. No.: 09/099,337

[22] Filed: Jun. 18, 1998

[51] Int. Cl.[7] .......................... G01N 29/10; G01N 29/04
[52] U.S. Cl. ................................. 73/621; 73/633; 73/641
[58] Field of Search ............................ 73/618, 620, 621, 73/622, 624, 625, 632, 633, 640, 641, 623, 628, 629; 600/409, 437, 424

[56] References Cited

U.S. PATENT DOCUMENTS

| | | | |
|---|---|---|---|
| 3,798,961 | 3/1974 | Flambard et al. | 73/71.5 |
| 3,844,164 | 10/1974 | Romere | 73/67.8 |
| 3,983,474 | 9/1976 | Kuipers | 324/41 |
| 4,480,485 | 11/1984 | Bradshaw et al. | 73/861.28 |
| 4,506,549 | 3/1985 | Thome | 73/582 |
| 4,541,064 | 9/1985 | Livingston | 364/552 |
| 4,625,557 | 12/1986 | Rutherford | 73/635 |
| 4,700,045 | 10/1987 | Merry et al. | 219/121 |
| 4,880,009 | 11/1989 | Yanagawa | 128/660.09 |
| 4,958,639 | 9/1990 | Uchiyama et al. | 128/660.03 |
| 4,980,871 | 12/1990 | Sieber et al. | 367/127 |
| 5,195,519 | 3/1993 | Angelsen | 128/660.01 |
| 5,211,167 | 5/1993 | Amenomori | 128/660.04 |
| 5,255,681 | 10/1993 | Ishimura et al. | 128/660.09 |
| 5,307,816 | 5/1994 | Hashimoto et al. | 128/660.03 |
| 5,339,259 | 8/1994 | Puma et al. | 364/559 |
| 5,361,768 | 11/1994 | Webler et al. | 128/660.09 |
| 5,390,674 | 2/1995 | Robinson et al. | 128/660.07 |
| 5,398,689 | 3/1995 | Connor et al. | 128/662.03 |
| 5,398,691 | 3/1995 | Martin et al. | 128/662.06 |
| 5,402,793 | 4/1995 | Gruner et al. | 128/660.1 |
| 5,417,216 | 5/1995 | Tanaka | 128/660.1 |
| 5,419,334 | 5/1995 | Miyagawa | 128/662.06 |
| 5,454,267 | 10/1995 | Moreau et al. | 73/623 |
| 5,474,225 | 12/1995 | Geier et al. | 228/104 |
| 5,622,170 | 4/1997 | Schulz | 128/653.1 |

OTHER PUBLICATIONS

R.L. Watkin, et al., "Three Dimensional Reconstruction and Enhancement of Arbitrarily Oriented and Positioned 2D Medical Ultrasonic Images." Conference Proceedings: 1993 Canadian Conference on Electrical and Computer Engineering, vol. II, ed. V.K. Bhargara, IEEE, p. 1188–1195 (1993).

*Primary Examiner*—Helen C. Kwok
*Attorney, Agent, or Firm*—Virginia B. Caress; William R. Moser; Paul A. Gottlieb

[57] ABSTRACT

The present invention relates to an ultrasonic scanner system and method for the imaging of a part system, the scanner comprising: a probe assembly spaced apart from the surface of the part including at least two tracking signals for emitting radiation and a transmitter for emitting ultrasonic waves onto a surface in order to induce at least a portion of the waves to be reflected from the part, at least one detector for receiving the radiation wherein the detector is positioned to receive the radiation from the tracking signals, an analyzer for recognizing a three-dimensional location of the tracking signals based on the emitted radiation, a differential converter for generating an output signal representative of the waveform of the reflected waves, and a device such as a computer for relating said tracking signal location with the output signal and projecting an image of the resulting data. The scanner and method are particularly useful to acquire ultrasonic inspection data by scanning the probe over a complex part surface in an arbitrary scanning pattern.

22 Claims, 6 Drawing Sheets

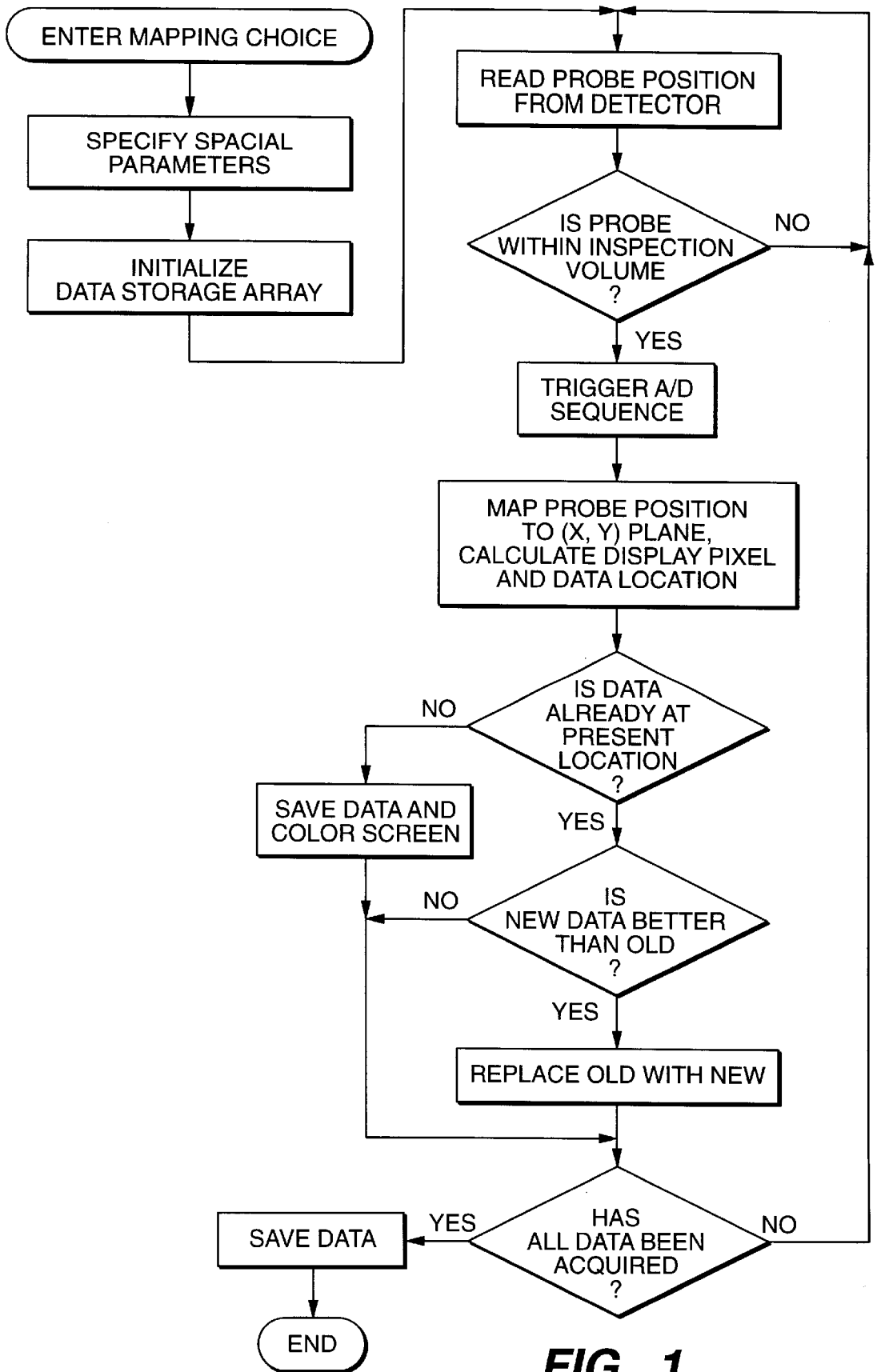
FIG._1

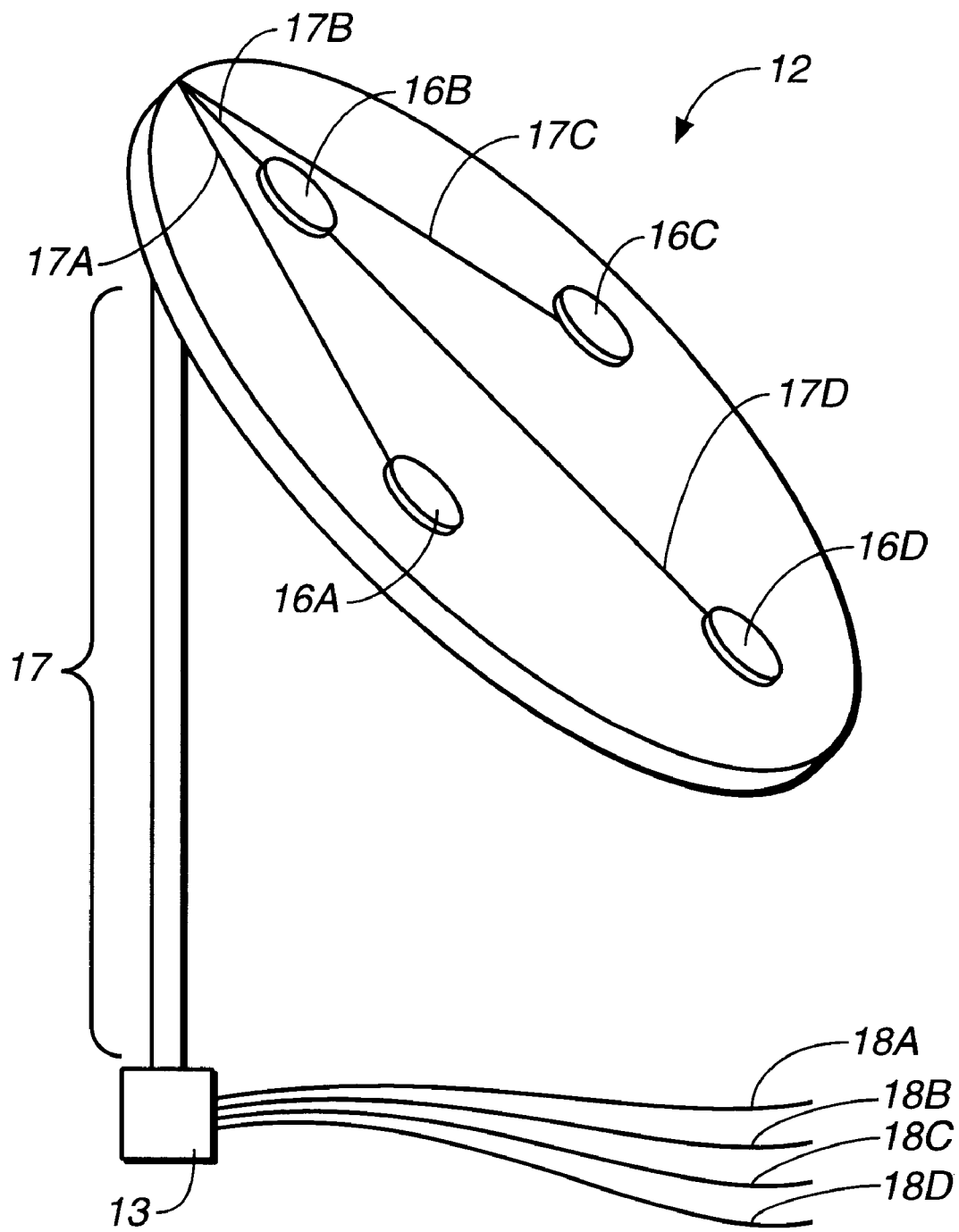
FIG._2

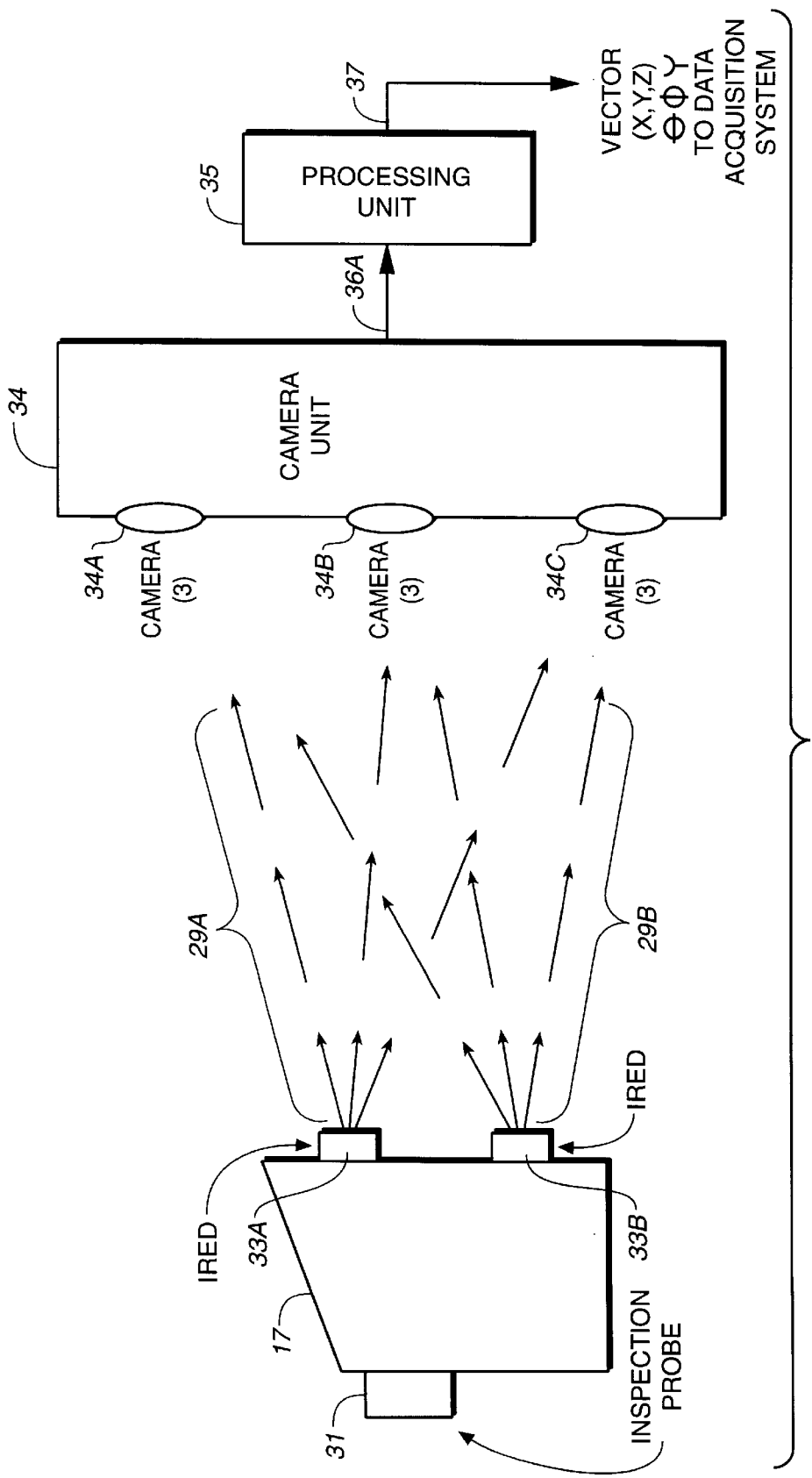
FIG._2A

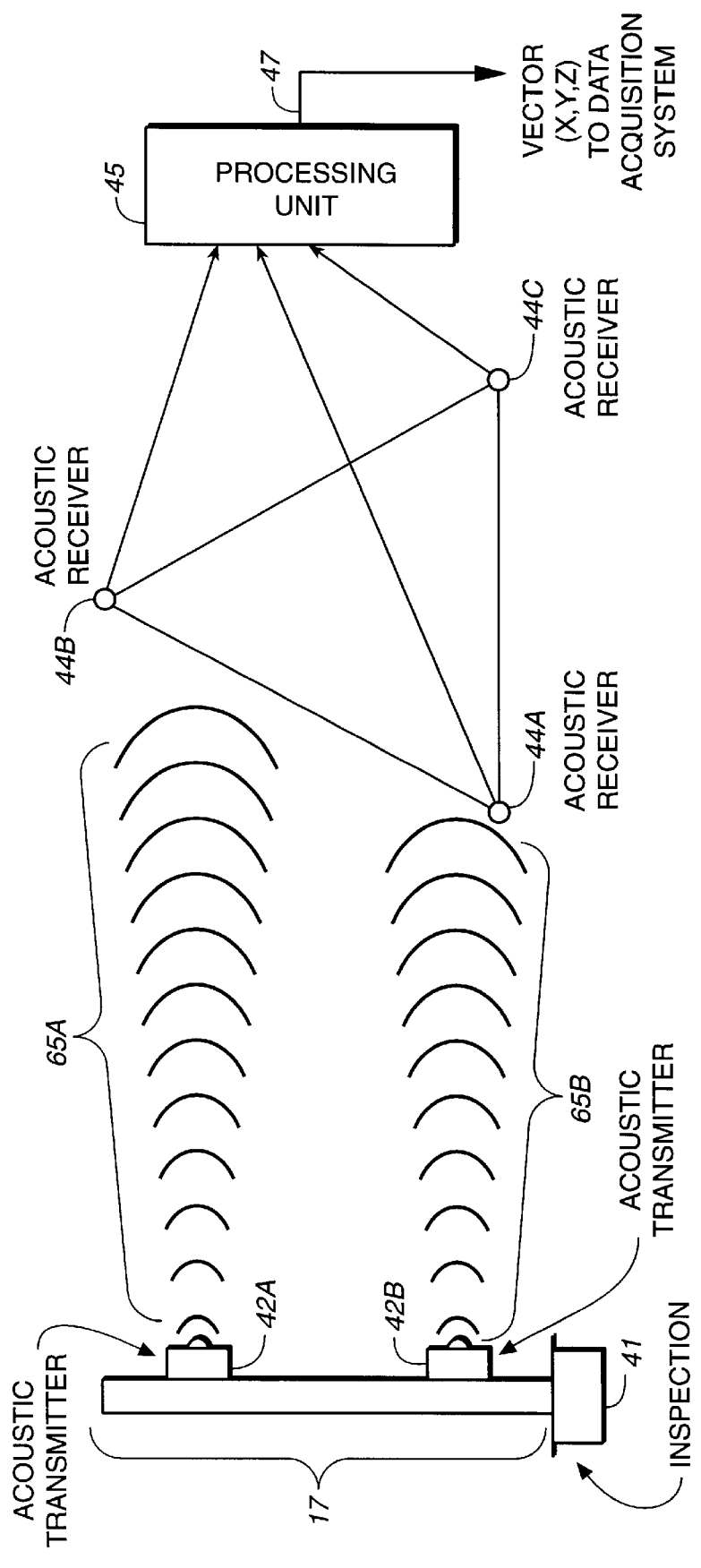
FIG._2B

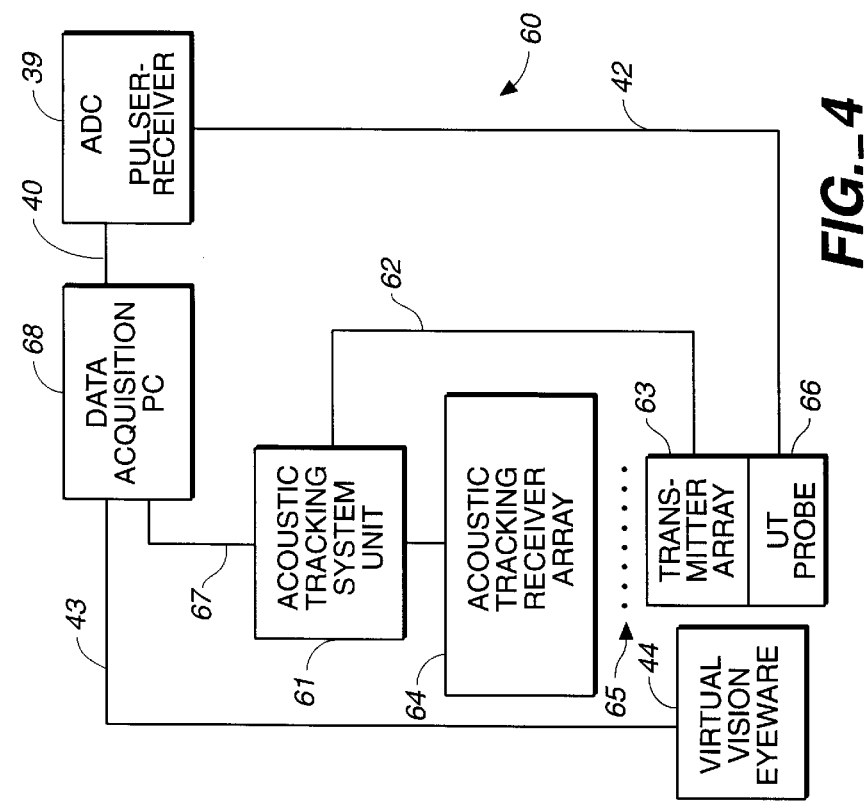
FIG._4
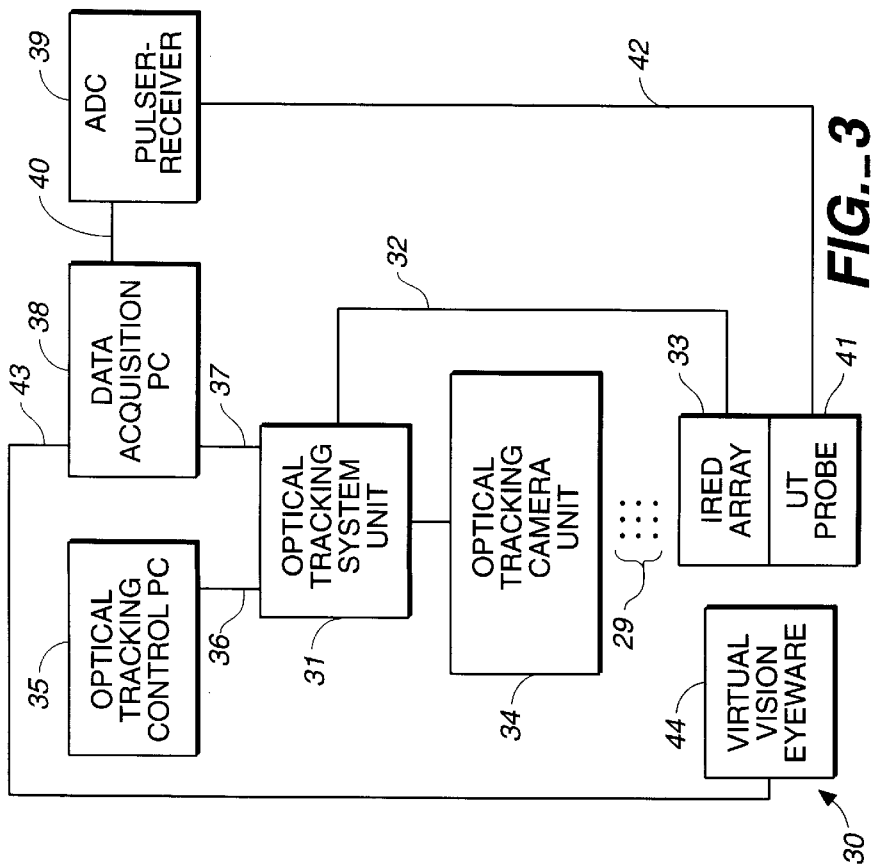
FIG._3

FREE MOTION SCANNING SYSTEM

BACKGROUND OF THE INVENTION

1. Field of the Invention

The present invention concerns an ultrasonic scanner and method for imaging the surface of a part. The present invention is particularly useful in the energy production area where location of defects in equipment is usually difficult using any nondestructive analysis procedure presently in the art.

2. Description of Related Art

The energy of sound waves is useful for checking the condition of materials. For example, ultrasonic energy may by used to detect the presence of flaws. Ultrasonics is advantageous over other destructive methods of testing materials for defects. In destructive testing, defects are made apparent by stressing the part, for example, by bending or tension until any cracks present on the part break open. By comparison, ultrasound is at such a low intensity that the part does not become damaged.

During ultrasonic testing, ultrasonic waves are transmitted from a transmitter on a probe into the part and then returning waves are received for analysis of the information it carries. In this manner, inspection data is obtained over a defined spatial sampling grid on the surface of a three-dimensional part. This data is stored in a computer's memory for subsequent analysis. The sound pressure distribution of the reflected waves are transferred into a visual image. During analysis, the spatial relationships between reflections of ultrasound from within the part are readily apparent in the image. For general information regarding ultrasonic instrumentation, See J. Krautkramer, et al., *Ultrasonic Testing of Materials,* 4th Ed. Springer-Verlag, N.Y. 1990 and D. Christensen, Ultrasonic Bioinstrumentation, John Wiley & Sons, Inc., N.Y., 1988.

Ultrasonic imaging requires a method to track the position of the transmitting probe such that the system can recognize when the probe is at a spatial sampling point and to obtain UT data there. Probe position feedback is often accomplished through position encoders mounted to a track assembly which is itself mounted to the part, See, for example, U.S. Pat. No. 4,700,045.

In the field of part inspection, the object to be tested often includes many non-uniform shapes and sizes, such as nozzles, valves, etc. Scanners which include track assemblies suffer from significant limitations in imaging such complex surfaces. Each track assembly can operate on at most a narrow range of part geometries. Therefore, fabrication of a special purpose track assembly is required for each new complex part to be inspected. Development of these track assemblies is an expensive and time consuming process. In addition, track assemblies generally restrict the motion of the probe to linear trajectories. In use, this track scanner is moved linearly followed by orthogonal increments and repeat of the linear motion. But any installed projection on the part surface limits the ability of the track assembly to complete the desired scan.

Some scanners are not mounted on a track, as in the medical diagnostics industry. However, these ultrasonic devices collect only a limited amount of data and are not efficient in imaging complex parts. These scanners obtain two-dimensional information about the position of the probe, and thus collect only two-dimensional data from the part being inspected. Computers fill-in missing information to create a three-dimensional image. Reconstruction requires sophisticated gap-filling interpolation algorithms, image resampling and image enhancements. See, for example, Watkin, et al., *Three-dimensional Reconstruction and Enhancement of Arbitrarily Oriented and Positioned 2D Medical Ultrasonic Images,* 1993 Canadian Conference on Electrical and Computer Engineering, pp. 1188–1195. Such reconstructed three-dimensional images lack accuracy.

Similarly, in Martin, et al. U.S. Pat. No. 5,398,691 a free standing probe is made to rotate in a two-dimensional coordinate system and is translated into three-dimensions relative to the space defined by a magnetic field generator. On the other hand, in the present invention, the probe is moved without constraint in three dimensions and the as measured probe location is used by the system software to control the inspection data acquisition process. The present invention has the advantage, therefore, that data acquisition is unconstrained by the three dimensional configuration of the part nor by probe motion and trajectory.

All references, articles, patents, patent applications, standards and the like cited herein are incorporated herein by reference in their entirety.

There is, therefore, a continuing need for ultrasonic scanners and methods which allow for accurate inspection of complex parts. The scanners should collect three-dimensional data which can be conveniently converted to a detailed two-dimensional image. Furthermore, the probe position should be monitored in a configuration which avoids the necessity of track assemblies. The present invention accomplishes these objectives.

SUMMARY OF THE INVENTION

The present invention allows for inspection of a large variety of different parts with complex surface shapes, e.g. valves, reactor vessel nozzles, fittings, welds, forgings, and the like. The present ultrasonic device tracks a three- dimensional position of a free-motion probe to gather detailed information about the part of interest. With the present invention, the necessity of reconstructing a two-dimensional image into a three-dimensional image is avoided. Thus, the present scanner provides more accurate and detailed information than scanners which require image reconstruction.

Unlike conventional mounted track scanning systems, the present invention also allows for inspecting of complex parts without having to design and fabricate a new scanner or track assembly for each new part configuration or differently sized part. Instead, with the present invention all that is needed to adapt the system to a new part configuration is relatively inexpensive software which can be quickly implemented. Thus, the present invention conserves time and expenses when compared to conventional scanners used to inspect parts.

The present invention also allows the scanning to be performed in an arbitrary pattern over the surface. In comparison to conventional scanners, the motion of the probe is not limited to a linear path. Several benefits thus arise from the freedom of motion. First, the operator can better locate defects on and within the part surface by making an initial scan and then investigating potential defects in greater detail. Second, the present invention provides greater freedom to avoid interferences on the part surface during the scanning process. For example, it may be desirable to avoid a welded nozzle present in close proximity to the weld being inspected. Track scanning assemblies, on the other hand, cannot easily move around these types of interferences.

The present invention relates to an ultrasonic scanner system and method for the imaging of a part surface, the scanner system comprising:

a probe assembly spaced apart from the surface including at least two tracking signal emitters for emitting electromagnetic or mechanical radiation and a transmitter for emitting ultrasonic waves onto a surface in order to induce at least a portion of the ultrasonic waves to be reflected from the surface, at least one detector for receiving the electromagnetic or mechanical radiation wherein the detector is positioned to receive this radiation from the tracking signals, an analyzing means for recognizing a three-dimensional probe location based on the emitted electromagnetic or mechanical radiation of the tracking signals and mapping the probe location to a two-dimensional vector, a differential conversion means for generating an output signal representative of the waveform of the reflected ultrasonic waves, and a means for relating said probe location with the output signal and projecting an image of the resulting data.

In another aspect, the present invention relates to a method for imaging a surface using a free motion scanner system including a probe assembly with at least two tracking signals emitting electromagnetic or mechanical radiation therefrom, the method comprising:

moving the probe assembly in a free motion over the surface to be imaged, emitting electromagnetic or mechanical radiation from the tracking signal emitters, determining a three-dimensional probe location from said electromagnetic or mechanical radiation, mapping the probe location to a two-dimensional vector, projecting ultrasonic waves from the probe assembly in order to induce reflected wave emission from the surface, generating a waveform in response to the reflected wave emissions, and producing an output signal representative of the waveform relative to the tracking signal location.

The scanner and method are particularly useful to acquire ultrasonic inspection data by scanning the probe over a complex part surface in an arbitrary scanning pattern. The data can be interpreted to identify defects, irregularities, non-uniformities, and the like on the surface of the object and within the object.

BRIEF DESCRIPTION OF THE DRAWINGS

FIG. 1 is a schematic representation of the operation (flow diagram) of the free motion scanning method performed according to the present invention.

FIG. 2 is a schematic representation of a probe assembly of the present invention.

FIG. 2A is a schematic representation of the operation of the probe assembly in an optical system.

FIG. 2B is a schematic representation of the operation of the probe assembly of an acoustic (sound) system.

FIG. 3 is a block schematic representation of a specific embodiment of the present invention including infrared light emitting diodes as the tracking signal emitters.

FIG. 4 is a block schematic representation of a specific embodiment of the present invention including acoustic transmitters as the tracking signals emitters.

DETAILED DESCRIPTION OF THE INVENTION AND PREFERRED EMBODIMENTS

Definitions

Figure 5:
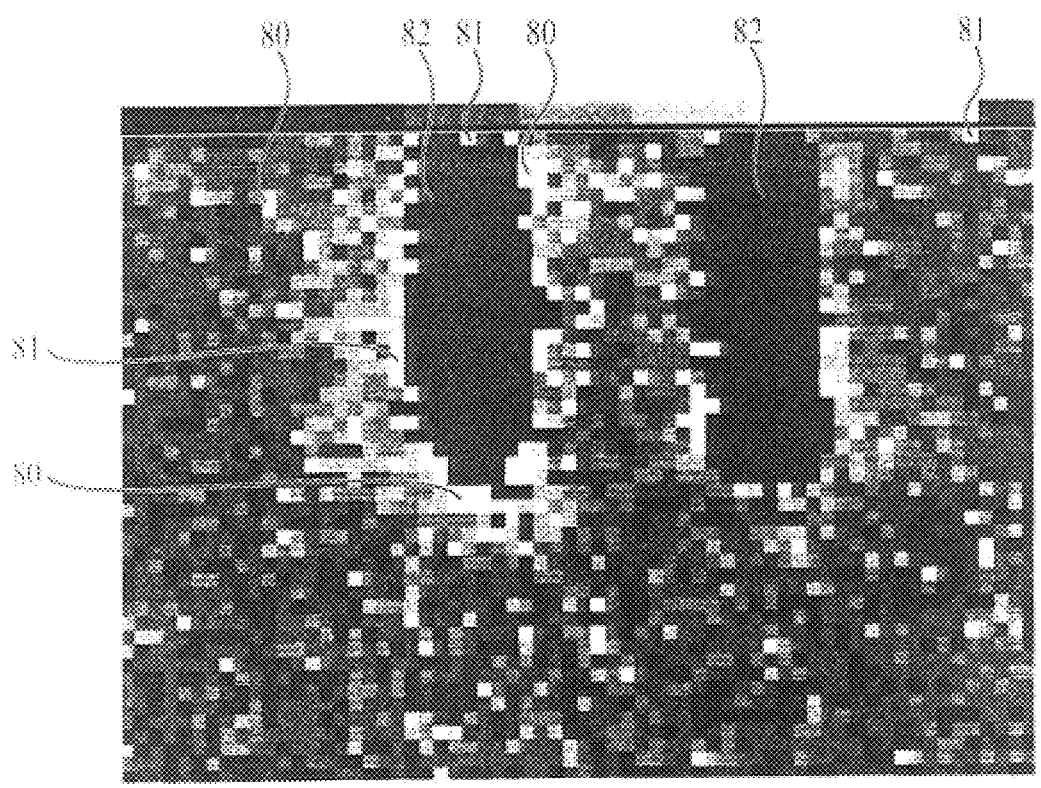
FIG. 5 is a computer generated image of a plate weld containing artificial defects obtained by using the present invention.

As used herein:

"Infrared light" refers to electromagnetic radiation which is outside of the visible range and close to the red end of the spectrum at wavelengths ranging from $10^3$ to $10^5$ microns.

"Acoustic waves" refers to mechanical radiation which is at frequencies ranging from 0 to 20 KHz.

"Ultrasonic waves" are acoustic waves with frequencies above those which can be detected by the ear, e.g. from about 20 KHz to several hundred MHz.

"Part" refers to any three-dimensional object to be examined. The term part includes, but is not limited to, valves, fittings, nozzles, welds, pipes, lines, forgings, and the like.

The present invention concerns a free-motion ultrasonic scanning device and method of its use in inspection of three-dimensional part surfaces. In general, the device includes a probe assembly comprising multiple tracking signal emitters and a transmitter. FIG. 1 is a flow diagram which describes the sequence of steps used in the present method. The tracking signals emitters are configured to release electromagnetic or mechanical radiation which is received by a detector. (See FIGS. 2A, 2B, 3 and 4 for more detail). An analyzing means collects the information from the detector and determines the three-dimensional position of the probe assembly and maps it to a two-dimensional vector. The transmitter emits ultrasonic waves onto a surface in order to cause reflection of the waves from the surface. A differential converter is operative to produce an output signal of the resulting waveform and a relating and imaging means relates the waveform data with the probe assembly position to create a two-dimensional image of the surface.

Typically the acoustic free motion scanning system is lighter in weight and occupies a smaller operational space than the optical system. Thus, the acoustic system is suitable for use in tight spaces, such as reactor compartments and the bulkier optical system is suitable for inspection of components with relatively open access, such as those on a shop floor or in large spaces.

The probe, system and method are described with reference to FIGS. 2, 2A, 2B, 3 and 4. The ultrasonic probe assembly 12 of the scanner, as shown in FIG. 2, includes the ultrasonic probe 13, rigid body 17 which separates and positions transmitters (the infrared emitting diodes) on the probe, transmitters 16A, 16B, 16C and 16D of infrared waves on a platform 19 and a transducer. The transmitters 16A, 16B, 16C and 16D are each connected electrical to separate wires 17A, 17B, 17C and 17D respectively which can be inside or outside of rod 17, and which become wires 18A, 18B, 18C and 18D respectively to the detection system. The probe assembly is of any convenient dimensions depending on, for example, the size of the part and space available for the probe. The probe is located proximal the surface of the part. The distance between probe assembly and surface depends on various scanning factors, such as strength of the transmitter and tracking signals, sensitivity of the system, shape of the part and the operator defined tolerance. The distance should be an amount that allows for optimal visualization of the surface. The space between the probe assembly and surface to be analyzed can be any medium, such as air, water, and preferably is air.

Tracking signal emitters are located directly on the probe assembly 12, or optionally, the probe assembly further includes a rigid body to which the signal emitters are affixed. The tracking signal emitters may be of any convenient transmitter of electromagnetic or mechanical radiation. In one preferred embodiment FIG. 2, the signal emitters are infrared light emitting diodes (IRED's) and emit infrared (IR) light (also see FIG. 2A). In another preferred embodiment, the tracking signals are from acoustic transmitters (42A and 42B) which transmit bursts of acoustic waves (65A and 65B) from between about 20 to 50 KHz, typically about 20 to 30 KHz and preferably about 20 KHz (FIG. 2B). Other such transmitters may include transmitters of visual light, and the like.

The number of tracking signal emitters on the probe varies and is at least two, depending on the type of signals employed and the size of the probe. For example, where the probe assembly includes acoustic signal emitters, the number of signal emitters are two and if optical signals are used, one or more signal emitters are present. The signal emitters may be in any convenient configuration on the probe assembly with respect to each other. Typically, where IRED's are implemented, the signal emitters are in a linear array.

Referring specifically to FIGS. 2A and 2B, three detectors are positioned to receive the radiation. Any appropriate type of detector is employed depending on the type of radiation detected. For example, where optical energy, i.e. infrared, is emitted, the detectors are cameras which create an image of each IRED. Where acoustic waves are emitted, the detectors are acoustic receivers. The detectors are located in non-contacting proximity to the probe assembly at a distance and configuration that allows for optimal detection of the radiation. In one embodiment, three acoustic receivers are in a triangular array. The radiation detectors determine the location of each signal emitters within a plane based on the detected radiation and transfer the information to an analyzing means.

In FIG. 2A (which includes FIG. 2) inspection probe 31 is connected to the optical probes 33A and 33B by a rigid body 17. Each optical probe emits infrared light which is transmitted to analyzing cameras 34A, 34B, and 34C in the camera unit 34. The electrical output of the camera unit 34 is transmitted to processing unit 35 via line(s) 36A. The processed data is conveyed via line 37 to the data acquisition system in terms of vectors x,y,z and θ, ψ and φ.

In FIG. 2B, inspection probe 41 is connected to the acoustic probe 42A and 42B by rigid body 17. The acoustic probes each emit acoustic energy 65A and 65B which is detected by acoustic receivers 44A, 44B and 44C. The electrical output of the receiver is transmitted to processing unit 45. The processed data is then conveyed via line 47 to the data acquisition system.

The analyzing means, such as a host computer determines the intersection of the planes from the tracking signals. The analyzing means outputs the position vector and orientation of an arbitrary point defined in relation to the fixed signals. The point may be determined by the difference in time of arrival of the transmitter emissions, especially in acoustic systems. In some embodiments, the point is the endpoint of the transmitter probe body and the known probe dimensions are used to determine the location of the endpoint.

The efficiency of the determined orientation of the point may be within six degrees of freedom, e.g. three linear and three rotational, when optical radiation with more than two signal emitters is used. Thus, optical systems have potential for high tracking accuracy. When acoustic systems are utilized, three degrees of motion are tracked, e.g. three linear points.

When the probe is positioned within an operator defined tolerance, in order to induce the transmitter to emit ultrasonic waves, a relating and imaging means such as a computer receives the information regarding the tracked probe position from the analyzing means via a serial port. The computer runs a terminate and stay resident program and receives the tracked position as if it were a keyboard input. The computer, preferably a personal computer, maps a two-dimensional vector indicating probe position from the three-dimensional position vector. The computer also triggers a pulser located within the computer casing to release a voltage of electricity across the transmitter at an appropriate frequency to create the desired excitation of the transmitter.

The transmitter which emits ultrasonic waves is mounted onto the probe assembly. The position of the transmitter coincides with the point determined relative to the location of the tracking signal emitters, as described above.

The transmitter may be any conventional means for generating ultrasonic waves, such as piezoelectric crystals and ceramics, and preferably piezoelectric crystals, e.g. quartz, barium titanate, lead zirconium titanate (PZT), poly (vinylidene fluoride) (PVDF), or the like. In use, the piezoelectric crystals change electrical excitation into motion and pressure.

In order to enhance the definition of the part surface, the scanner optionally includes a lens or other focusing scheme such as a spherical reflector. The lens will converge the radiating beam from the transmitter into a spot at the focal plane of the lens on the part surface. The lens is made of material, such as polystyrene, with phase velocity greater than the surrounding medium, i.e. water or air. The ultrasonic waves then contact the surface and at least a portion of the waves reflect back away from the surface.

A transducer receives the waves reflected from the surface and outputs corresponding electrical signals. The transducer may be any conventional means for receiving and generating signals, such as piezoelectric crystals which change the impinging pressure fields into strain and resulting voltage. Optionally, the transducer is the same as the transmitter and thus acts to emit ultrasonic waves and receive reflected waves.

A differential converter accepts the electrical signals from the transmitter as a waveform and outputs a signal which represents the waveform. The differential converter may be an analog-to-digital converter (ADC) to receive an analog signal indicative of the waveform and to output a digital signal.

The relating and imaging means, i.e. computer, retrieves the waveform from ADC memory and writes the waveform data, probe position, mapped position, peak signal amplitude and time of flight to peak amplitude to random access memory (RAM). The computer creates an image which depicts the relationship of the reflected waveform and the probe position. The computer may include a screen, such as a video display terminal (VDT) to image the results.

The pixels on the screen correspond to the mapped two-dimensional vector. In a preferred embodiment, the pixels are colored in relation to the maximum amplitude of the ultrasonic wave signal. A cursor provided on the screen is optionally displayed during scanning to indicate the relative position of the probe in the scanning area. In use, the operator scans the surface of the part, painting the computer screen with color until all pixels have been colored, indicating scanning is complete.

In one embodiment, in order to assist the operator, remote vision eyeware is included with the scanner. The remote vision eyeware connects in parallel with the computer monitor and projects an image of the computer screen into one eye of the operator. Thus, the operator may view the scanning of the part surface with an image of the computer screen superimposed in the operator's vision.

In using the present scanner to inspect an object, the operator follows the step-by-step process as depicted in the flow diagram of FIG. 1. To initiate the process, the user enters a mapping choice from a menu of choices into a computer, usually via a keyboard. The mapping choice indicates the shape and size of the part to be inspected. For example, the mapping choice may be a generic cone, a disk, an inlet nozzle flange, or the like. The computer is pre-programmed to initialize a data storage array at this point in order to allow for the storage of incoming information during the probing process.

Next, the user places the probe into position and activates the tracking signal emitters on the probe to release electromagnetic or mechanical radiation towards a detector. The radiation is received by the detector which automatically transmits the information into the computer. The information is read by the computer as three-dimensional values. To evaluate whether the probe position is in the appropriate space proximal the part to be inspected, the computer compares the values to spacial parameters designated by the previously entered mapping choice. The computer indicates to the user if the probe is not within the inspection volume defined by the parameters. In this case, the user moves the probe to a new position and the probe position is reread by the computer until the appropriate position is achieved. When the probe is within the inspection volume of interest, the probe releases ultrasonic waves toward the object to be inspected.

Signals generated as a result of reflected waves from the object are received by the analog-to-digital converter which then outputs a digital signal to the computer. The computer then automatically converts the three-dimensional (X-Y-Z) probe position onto a two-dimensional (X-Y) plane and calculates the corresponding display pixel and data location using the digital signals. Table 1 shows one algorithm which is used by the computer to interpret probe position data. Table 2 shows a different algorithm which is used by the computer to interpret probe position data.

TABLE 1

```
POINT CUniversalUTView:: MapLocation (length_3D* Vector. CString* Shape)
{
    POINT XY_Mapping:
    if (*Shape == "Plate") {
        XY_Mapping.x = (long) ((Vector->x - ScanStart.x)/IndexIncrement):
        XY_Mapping.y = (long) ((Vector->y - ScanStart.y)/ScanIncrement):
        return (XY_Mapping):
    }
    if (*Shape == "Disk") {
        XY_Mapping.x = (long) ((atan2(Vector->y.Vector->x)-atan2 (ScanStart.y.ScanStart.x)/IndexIncrement):
        XY_Mapping.y = (long) ((_hypot(Vector->x.Vector->y- _hypot(ScanStart.x.ScanStart.y))/ScanIncrement):
        return (XY_Mapping):
    }
    if (*Shape == "Cylinder") {
        XY_Mapping.x = (long) ((atan2(Vector->y.Vector->x)-atan2 (ScanStart.y.ScanStart.x)/IndexIncrement):
        XY_Mapping.y = (long) ((Vector->z-ScanStart.z)/(cos(14.0*PI/180.0)*ScanIncrement)):
        return (XY_Mapping):
    }
    AfxMessageBox ("Corrupted Part Shape passed to MapLocation routine"):
    return (XY_Mapping):
}
```

TABLE 2

```
POINT CAcquireUUTView: :MapLocation(Length_3D " Vector. CString " Shape. CAcquireUUTDoc " pDoc)
{
    POINT     XY_Mapping = {-1.-1}:
    if("Shape = = "Plate") {
        XY_Mapping.x = (long] ((Vector->x - pDoc- >ScanStart.x]/pDoc- >IndexIncrement):
        XY_Mapping.y = (long] ((Vector->y - pDoc->ScanStart.y)/pDoc->ScanIncrement):
        return (XY_Mapping):
}
if(*Shape = = "Disk") (
    XY_Mapping.x = (long) ((atan2(Vector->y.Vector->x)-stan2(pDoc->ScanStart.y.pDoc->ScanStart.x))/pDoc->IndexIncrement):
    XY_Mapping.y = (long) ((_bypot(Vector->x.Vector->y)-_hypot(pDoc->ScanStart.x.pDoc->ScanStart.y))/pDoc->ScanIncrement):
    return XY_Mapping:
}
if(*Shape = = "Cylinder") {
XY_Mapping.x = (long) ((atan2(Vector->y.Vector->x)-atan2(pDoc->ScanStart.y.pDoc->ScanStart.x))/pDoc->IndexIncrement):
XY_Mapping.y = (long) ((Vector->z-pDoc->ScanStart.x)/(cos(14.0*PI/180.0)*pDoc->ScanIncrement)):
return XY_Mapping:
}
if(*Shape = = "Generic Plate") (
    // added for generic mapping to prevent the replacement of coordinate data
    length_3D temp Vector:
    tempVector.x = Vector->x:
    tempVector.y = Vector->y:
    tempVector.z = Vector->z:
    //////////////////////////////////////////////////
    // Translate to origin
    tempVector.x = tempVector.x - pDoc->TranslationVector.x:
```

TABLE 2-continued

```
tempVector.y = tempVector.y - pDoc->TranslationVector.y:
tempVector.z = tempVector.z - pDoc->TranslationVector.z:
//
// Rotate about Z axis
holdx = tempVector.x:
holdy = tempVector.y:
tempVector.x = (float)((cos(pDoc->TransformationAngles.z)*holdx) - (sin(pDoc->TransformationAngles.z)*holdy)):
tempVector.y = (float)((sin(pDoc->TransformationAngles.z)*holdx) + (cos(pDoc->TransformationAngles.z)*holdy)):
// Rotate About Y-axis
holdx = tempVector.x:
holdx = tempVector.z:
tempvector.x = (float)((cos(pDoc->TransformationAngles.y)*holdx) + (sin(pDoc->TransformationAngles.y)*holdz)):
tempVector.z = (float)((cos(pDoc->TransformationAngles.y)*holdz) - (sin(pDoc->TransformationAngles.y)*holdx)):
//
// Rotate About X-axis
holdy = tempVector.y:
holdz = tempVector.z:
tempVector.y = (float)((cos(pDoc->TransformationAngles.x)*holdy) - (sin(pDoc->TransformationAngles.x)*holdz)):
tempVector.z = (float)((sin(pDoc->TransformationAngles.x)*holdy) + (cos(pDoc->TransformationAngles.x)*holdz)):
//
XY_Mapping.x = (long) ((tempVector.x-pDoc->MapStart.x)/pDoc->IndexIncrement):
XY_Mapping.y = (long) ((tempVector.x-pdoc->MapStart.y)/pDoc->ScanIncrement):
return XY_Mapping:
}
if("Shape = = "Generic Sphere") {
//added for generic mapping to prevent the replacement of coordinate data
length_3D tempVector:
tempVector.x = Vector->x:
tempVector.y = Vector->y:
tempVector.z = Vector->z:
//////////////////////////////////////////////////////////////
// Translate to origin
tempVector.x = tempVector.x - pDoc->ObjectCenter.x:
tempVector.y = tempVector.y - pDoc->ObjectCenter.y:
tempVector.z = tempVector.z - pDoc->ObjectCenter.z:
//
// Rotate about Z axis
holdx = tempVector.x:
holdy = tempVector.y:
tempVector.x = (float)((cos(pDoc->TransformationAngles.z)*holdx) - (sin(pDoc->TransformationAngles.z)*holdy)):
tempVector.y = (float)((sin(pDoc->TransformationAngles.z)*holdx) + (cos(pDoc->TransformationAngles.z)*holdy)):
// Rotate About Y-axis
holdx = tempVector.x:
holdz = tempVector.z:
tempVector.x = (float)((cos(pDoc->TransformationAngles.y)*holdx) + (sin(pDoc->TransformationAngles.y)*holdz)):
tempVector.z = (float)((cos(pDoc->TransformationAngles.y)*holdz) - (sin(pDoc->TransformationAngles.y)*holdx)):
//
// Rotate About X-axis
holdy = tempVector.y:
holdz = tempVector.z:
tempVector.y = (float)((cos(pDoc->TransformationAngles.x)*holdy) - (sin(pDoc->TransformationAngles.x)*holdx)):
tempVector.z = (float)((sin(pDoc->TransformationAngles.x)*holdy) + (cos(pDoc->TransformationAngles.x)*holdz)):
//
holdx = tempVector.x:
holdy = tempVector.y:
tempVector.x = (float)(atan(holdy/holdx)*pDoc->ObjectRadius):
tempVector.y = (float)(atan((tempVector.z)/holdx)*pDoc->ObjectRadius):
XY_Mapping.x = (long) ((tempVector.x-pDoc->MapStart.x)/pDoc->IoderIncrement):
XY_Mapping.y = (long) ((tempVector.y-pDoc->MapStart.y)/pDoc->ScanIncrement):
return XY_Mapping:
}
if(*Shape = = "Generic Cylinder") {
// added for generic mapping to prevent the replacement of coordinate data
length_3D tempVector:
tempVector.x = Vector->x:
tempVector.y = Vector->y:
tempVector.z = Vector->x:
//////////////////////////////////////////////////////////////
// Translate to origin
tempVector.x = tempVector.x - pDoc->TranslationVector.x:
tempVector.y = tempVector.y - pDoc->TranslationVector.y:
tempVector.z = tempVector.z - pDoc->TranslationVector.z:
//
// Rotate about Z axis
holdx = tempVector.x:
holdy = tempVector.y:
tempVector.x = (float)((cos(pDoc->TransformationAngles.z)*holdx) - (sin(pDoc->TransformationAngles.z)*holdy)):
tempVector.y = (float)((sin(pDoc->TransformationAngles.z)*holdx) + (cos(pDoc->TransformationAngles.z)*holdy)):
// Rotate About Y-axis
```

TABLE 2-continued

```
    holdx = tempVector.x:
    holdz = tempVector.z:
    tempVector.x = (float)((cos(pDoc->TransformationAngles.y)*holdx) + (sin(pDoc->TransformationAngles.y)*holdz)):
    tempVector.z = (float)((cos(pDoc->TransformationAngles.y)*holdz) - (sin(pDoc->TransformationAngles.y)*holdx));
    // Rotate About X-axis
    holdy = tempVector.y:
    holdz = tempVector.z:
    tempVector.y = (float)((cos(pDoc->TransformationAngles.x)*holdy) - (sin(pDoc->TransformationAngles.x)*holdz)):
    tempVector.z = (float)((sin(pDoc->TransformationAngles.x)*holdy) + (cos(pDoc->TransformationAngles.x)*holdz)):
    //
    holdx = tempVector.x:
    tempVector.x = tempVector.y:
    if((holdx<=0)&&(tempVector.z>=0))
        tempVector.y = ((float) (-1.0*atan(holdx/(tempVector.z))+22.0/14.0)*pDoc->ObjectRadius):
    else if((holdx<=0)&&(tempVector.z<=0))
        tempVector.y = ((float)(-1.0*atan(holdx/(tempVector.z))-22.0/14.0)*pDoc->ObjectRadius):
    else tempVector.y = (float)(atan((tempVector.z)/holdx)*pDoc->ObjectRadius):
    if((mapcorrection==1)&&(tempVector.y<(pDoc->MapStop.y-pDoc->ObjectRadius*44.0f/7.0f)))temp
    Vector.y*tempVector.y+(44.0f/7.0f)*pDoc->ObjectRadius;
    XY_Mapping.x = (long) ((tempVector.x-pDoc->MapStart.x)/pDoc->IndexIncrement):
    XY_Mapping.y = (long) ((tempVector.y-pDoc->MapStart.y)/pDoc->ScanIncrement):
return XY_Mapping:
}
if(*Shape == "Generic Core") (
// added for generic mapping to prevent the replacement of coordinate data
length_3D tempVector:
tempVector.x = Vector->x:
tempVector.y = Vector->y:
tempVector.z = Vector->z:
/////////////////////////////////////////////////////////////////////
// Translate to tip at origin
tempVector.x = tempVector.x - pDoc->TranslationVector.x:
tempVector.y = tempVector.y - pDoc->TranslationVector.y:
tempVector.z = tempVector.z - pDoc->TranslationVector.z:
// Rotate About Z-axis
holdx = tempVector.x:
holdy = tempVector.y:
tempVector.x = (float)((cos(pDoc->TransformationAngles.z)*holdx) - (sin(pDoc->TransformationAngles.x)*holdy)):
tempVector.y = (float)((sin(pDoc->TransformationAngles.z)*holdx) + (cos(pDoc->TransformationAngles.z)*holdy)):
//
// Rotate About Y-axis
holdx = tempVector.x:
holdz = tempVector.x:
tempVector.x = (float)((cos(pDoc->TransformationAngles.y)*holdx) + (sin(pDoc->TransformationAngles.y)*holdz)):
tempVector.z = (float)((cos(pDoc->TransformationAngles.y)*holdz) - (sin(pDoc->TransformationAngles.y)*holdx)):
//
// Rotate About X-axis
holdy = tempVector.y:
holdz = tempVector.z:
tempVector.y = (float)((cos(pDoc->TransformationAngles.x)*holdy) - (sin(pDoc->TransformationAngles.x)*holdz)):
tempVector.z = (float)((sin(pDoc->TransformationAngles.x)*holdy) + (cos(pDoc->TransformationAngles.x)*holdz)):
//
holdy = tempVector.y:
tempVector.x = (float)(tempVector.x/cos(pDoc->angle_of_cone)):
if(fabs(tempVector.z)<0.01f) tempVector.z = 0.0f: // needed to put very small starts at 0
// the following are the dependencies of quadrant
if((holdy<0)&&(tempVector.z>0))
    tempVector.y = (float)((22.0f/14.0f+fabs(atan(holdy/tempVector.z)))*pDoc->ObjectRadius):
else if((holdy<=0)&&(tempVector.z<=0))
    tempVector.y = (float)((22.0f/7.0f+fabs(atan((tempVector.z)/holdy)))*pDoc->ObjectRadius):
else if((holdy>0)&&(tempVector.z<0))
    tempVector.y = (float)((66.0f/14.0f+fabs(atan(holdy/tempVector.z)))"pDoc->ObjectRadius):
else tempVector.y = (float)(pDoc->ObjectRadius"atan((tempVector.z)/holdy)):
if((mapcorrection==Z)&&(tempVector.y< (pDoc->MapStop.y-pDoc->ObjectRadius*44.0f/7.0f))) tempVector.y=temp
Vector.y+(44.0f/7.0f)*pDoc->ObjectRadius:
XY_Mapping.x = (long) ((tempVector.x-pDoc->MapStart.x)/pDoc->IndexIncrement):
XY_Mapping.y = (long) ((tempVector.y-pDoc->MapStart.y)/pDoc->ScanIncrement):
return XY_Mapping:
}
// If none of the part shapes are recognized. stop the scan and notify the user.
pDoc->InterruptScan = TRUE:
AfxMessageBox("Corrupted Part Shape passed to MapLocation routine".MB_ICONSTOP):
return (XY_Mapping):
}
```

The computer then searches its memory to see if there are already been obtained, the computer compares the two data previously obtained data at the probe position. If data has sets and retains the set with the most relevant information. The information is saved and a screen depicting the data is colored.

The user finally determines if there is any additional information required of the inspection area. If more data is needed, the user moves the probe, the probe position is reread and the above steps are repeated. When scanning is complete, the computer transfers the inspection data from RAM to long term storage. The data is available to be analyzed at any subsequent time using conventional visual and signal processing techniques known in the art.

FIG. 3 shows a block schematic representation of one embodiment of scanner employing an optical system 30. In this embodiment, the optical tracking system 31 is connected by line 32 to IRED array 33 and triggers the release of infrared light 29 from the IRED array 33. The optical tracking camera unit 34 detects the presence of the infrared light 29 and creates an image of each IRED within a plane. The optical tracking system 31 feeds the camera image via line 36 to the optical tracking control personal computer (PC) 35 which solves for intersection of the planes to output to unit 31 the position and orientation of the probe assembly. The optical tracking system unit 31 provides the vector information via line 37 to the data acquisition PC 38 through a serial port. When the probe is in the appropriate position, the data acquisition PC 38 triggers the pulser-receiver 39 via line 40 which provides electrical signals via line 42 to the UT probe 41, initiating the release of ultrasonic waves. The probe receives the ultrasonic reflected waves and supplies corresponding electrical signals to the receiver 39. The signals are routed to the ADC receiver 39 which converts the analog signals to digital signals. The data acquisition PC 38 retrieves the digital data and relates the data to the two-dimension vector information mapped from the three-dimensional position vector and outputs a two-dimension image onto a screen via line 43. Virtual vision eyeware 44 can be used by the operator to view the image.

FIG. 4 shows a block schematic representation of another embodiment of scanner employing an acoustic tracking system 60. In this embodiment, the acoustic tracking system unit 61 triggers the release of acoustic waves via line 62 from the acoustic transmitter array 63. The acoustic tracking receiver array 64 detects the presence of the acoustic waves 65 and determines the differences in time of arrival of the transmitter emissions. The acoustic tracking system unit 61 calculates the location in space of the ultrasonic transmitter on the UT probe 66 and feeds the information via line 67 to the data acquisition PC 68 through a serial port. The data acquisition PC 68, running a terminate and stay resident program, receives the tracked position as if it were a keyboard input. The remaining operation of the acoustic system as shown in FIG. 4 is identical to that of the optical system represented in FIG. 3 described above.

In another embodiment of the present invention, the free motion scanner is implemented by using an articulated device employing motion encoders at each joint. A commercial device, known in the art is MicroScribe. An effective means to implement the free motion scanner is to mount an ultrasonic transducer to the stylus end of a MicroScribe device, and to interface the device to the data acquisition system through the serial port. The MicroScribe (e.g., MicroScribe 3DX™) is commercially available from Immersion Corporation, 2158 Paragon Drive, San Jose, Calif. 95131.

The following example is provided to be descriptive and explanatory only. It is not to be construed to be limiting in any way.

EXAMPLE 1

Scanning Plate Weld with Defects

A plate weld with two internal artificial defects is provided. The defects are located at depths of one-half and one and one-half inches, respectively, below the weld surface.

The probe assembly of FIG. 2 is moved in an arbitrary pattern over the surface of the plate along the weld as infrared radiation is emitted from IRED's arranged in a linear array on the rigid body of the probe assembly. Three cameras image the light from each IRED and determine the three-dimensional location of the IRED's within a plane. A host computer determines the position of a point which coincides with the probe transmitter and feeds the information to a personal computer. The computer commands the pulser to trigger the transmitter to release ultrasonic waves onto the weld surface. The surface then reflects back a portion of the waves to the transducer on the probe assembly, and a receiver captures the signals and passes them to an ADC. The personal computer retrieves the digital codes and relates the information to the probe position. An image of the surface (which may be color coded) is created.

The resulting image, as shown in FIG. 5, is coded in white, black and gray to represent the maximum amplitude of the ultrasonic reflected wave signal at each spatial sample point. A scale of amplitudes is denoted by the white, black and gray shades, where gray shade (80) represents low amplitudes, white (81) for medium amplitudes and, and black (82) for high amplitudes. FIG. 5 shows both of the artificial defects as black (82) regions, surrounded by lower amplitude white (81) and gray shade (80) as the defect is less fully within the path of the ultrasonic wave beam.

While only a few embodiments of the invention have been shown and described herein, it will become apparent to those skilled in the art that various modifications and changes can be made in the apparatus or the method to free motion scan part surfaces without departing from the spirit and scope of the present invention. All such modifications and changes coming within the scope of the appended claims are intended to be carried out hereby.

We claim:

1. A free motion scanner system for image inspection of an object, adapted for tracking a three dimensional position of a probe assembly which is moved over a surface of said object said scanner system comprising:

a probe assembly being movable without constraint in three dimensions over said surface, spaced apart from said surface, comprising at least two tracking signal emitters for emitting radiation and a transmitter for emitting ultrasonic waves onto said object in order to induce at least a portion of said ultrasonic waves to be reflected from said object;

at least one detector for receiving said radiation wherein said detector is positioned to receive said radiation from said tracking signal emitters;

an analyzing means for recognizing a three-dimensional probe assembly position based on said emitted radiation and for mapping said probe assembly position to a two-dimensional vector;

a differential conversion means for generating an output signal representative of a waveform of said reflected ultrasonic waves; and a means for relating said probe assembly position with said output signal to produce data, and projecting a two-dimensional image of the resulting said data, representing said object.

2. A scanner system according to claim 1, wherein said tracking signal emitters are infrared light emitting diodes (IRED).

3. A scanner system according to claim 2, wherein said at least one detector comprises cameras to image infrared light emitted from said infrared light emitting diodes.

4. A scanner system according to claim 1, wherein said tracking signal emitters are acoustic transmitters.

5. A scanner system according to claim 4, wherein said at least one detector comprises acoustic receivers for detecting acoustic waves emitted from said acoustic transmitters.

6. A scanner system according to claim 5, wherein said acoustic receivers comprise three acoustic receivers in a triangular array.

7. A scanner system according to claim 1, wherein the space between said probe assembly and said surface consists of air and said transmitter emits ultrasonic waves through said air onto said object.

8. A scanner system according to claim 1, wherein said object is selected from a vessel nozzle, valve body, fitting, weld, seam, or forging.

9. The scanner system according to claim 1, wherein said probe assembly comprises an articulated device wherein said tracking signal emitters comprise motion encoders.

10. A free motion ultrasonic scanner system for image inspection of an object adapted for tracking a three dimensional position of a probe assembly which is moved over a surface of said object said scanner system comprising:

a probe assembly being movable without constraint in three dimensions over said surface, spaced apart from said surface, comprising at least two tracking signal emitters for emitting tracking signals and a transmitter for emitting ultrasonic waves onto said object in order to induce at least a portion of said ultrasonic waves to be reflected from said object;

at least one detector for receiving said tracking signals wherein said at least one detector is positioned to receive said tracking signals from said tracking signal emitters;

an analyzing means for recognizing a three-dimensional location of said tracking signal emitters;

a pulser for electrically exciting said transmitter to emit ultrasonic waves onto said object in order to induce reflected ultrasonic wave emissions from said object;

a receiver for capturing a signal corresponding to said reflected ultrasonic wave emissions from said object;

an analog-to-digital converter for generating a digital output signal representative of a waveform of said reflected ultrasonic wave emissions; and a means for relating said three-dimensional location of said tracking signal emitters with said digital output signal and projecting an image of resulting data representing said object.

11. A scanner system according to claim 10, wherein said tracking signals are signals from infrared light emitting diodes (IRED).

12. A scanner system according to claim 11, wherein said at least one detector comprises cameras to image infrared light emitted from said infrared light emitting diodes.

13. A scanner system according to claim 10, wherein said tracking signal emitters are acoustic transmitters.

14. A scanner system according to claim 13, wherein said at least one detector comprises acoustic receivers for detecting acoustic waves emitted from said acoustic transmitters.

15. A scanner system according to claim 10, wherein the space between said probe assembly and said surface of said object consists of air and said transmitter emits ultrasonic waves through said air onto said object.

16. The scanner system according to claim 10, wherein said probe assembly comprises an articulated device wherein said tracking signal emitters comprise motion encoders.

17. A method of ultrasonic scanning of an object in an arbitrary pattern using a free motion scanner system including a probe assembly with at least two tracking signal emitters for emitting radiation and a transmitter for emitting ultrasonic radiation, the steps comprising:

moving said probe assembly in a free motion arbitrary pattern over a surface of said object;

emitting radiation from said tracking signal emitters;

determining a three-dimensional probe assembly location of said tracking signal emitters;

mapping said three-dimensional probe assembly location to a two-dimensional vector;

emitting ultrasonic waves from said transmitter on said probe assembly onto said object in order to induce reflected ultrasonic wave emissions from said object;

generating a waveform in response to said reflected ultrasonic wave emissions; and producing an output signal representative of said waveform relative to said probe assembly location.

18. A method according to claim 17, wherein said output signal is an image.

19. A method according to claim 17, wherein said ultrasonic wave emissions are projected through air from said probe assembly to said object.

20. A method according to claim 17, wherein said radiation is infrared light.

21. A method according to claim 17, wherein said radiation is an acoustic wave.

22. The method according to claim 17, wherein said probe assembly comprises an articulated device employing motion encoders, and said motion encoders emit tracking signal radiation.

* * * * *